(12) United States Patent
Hoctor et al.

(10) Patent No.: US 6,914,539 B2
(45) Date of Patent: Jul. 5, 2005

(54) SYSTEM AND METHOD FOR A LOW RATE, IN-BAND BROADCAST COMMUNICATION FOR MEDICAL TELEMETRY

(75) Inventors: Ralph Thomas Hoctor, Saratoga Springs, NY (US); John Erik Hershey, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 463 days.

(21) Appl. No.: 10/265,497

(22) Filed: Oct. 7, 2002

(65) Prior Publication Data

US 2004/0066312 A1 Apr. 8, 2004

(51) Int. Cl.[7] .............................................. G08C 15/06
(52) U.S. Cl. ............................ 340/870.12; 340/870.07; 340/870.01; 370/343; 370/344; 455/41.2; 455/507; 455/63.1
(58) Field of Search ....................... 340/870.07, 870.01, 340/870.12; 370/343, 344, 477; 455/41.2, 507, 63.1

(56) References Cited

U.S. PATENT DOCUMENTS

| 5,005,169 | A | | 4/1991 | Bronder et al. | |
|---|---|---|---|---|---|
| 6,154,500 | A | * | 11/2000 | Dorenbosch et al. | 375/259 |
| 6,389,087 | B1 | | 5/2002 | Heinonen et al. | |
| 6,400,679 | B1 | * | 6/2002 | Suzuki | 370/208 |
| 6,731,953 | B1 | * | 5/2004 | McGowan et al. | 455/561 |

* cited by examiner

*Primary Examiner*—Albert K. Wong
(74) *Attorney, Agent, or Firm*—Jean K. Testa; Christian G. Cabou

(57) ABSTRACT

A medical telemetry system includes a central station having a central station receiver and a central station transmitter that both operate on a frequency bandwidth having frequency multiplexed transmission channels and guard bands. A guard band separates each of the frequency-multiplexed transmission channels. The central station receiver wirelessly receives patient data from one of the frequency-multiplexed transmission channels. The central station transmitter wirelessly transmits control data information via each of the guard bands. At least one patient monitor is provided that includes a patient monitor receiver and a patient monitor transmitter that both operate on the frequency bandwidth. The patient monitor is wirelessly connected to the central station. The patient monitor receiver is configured for wirelessly receiving the control data information from the central station transmitter via the guard bands. The patient monitor transmitter is configured for wirelessly transmitting the patient data to the central station receiver via one of the frequency multiplexed transmission channels.

50 Claims, 5 Drawing Sheets

SYSTEM AND METHOD FOR A LOW RATE, IN-BAND BROADCAST COMMUNICATION FOR MEDICAL TELEMETRY

BACKGROUND OF THE INVENTION

The present invention relates generally to medical telemetry system and more specifically to a method and system for providing two-way communication between patient monitors and a central station where control channel information is transmitted using the pre-defined guardbands in transmission bandwidth.

In response to growing concerns about interference resulting from various transmissions (including digital television transmissions), the Federal Communications Commission (FCC) established the wireless medical telemetry service (WMTS) that dedicates bands of frequencies for interference-free operation of medical telemetry systems. The WMTS bands include 608 to 614 MHz, 1395 to 1400 MHz and 1427 to 1429.5 MHz.

Medical telemetry systems usually comprise a transmitter for transmitting electromagnetic signals and a receiver for receiving the electromagnetic signals from the transmitter. In the medical telemetry systems, the transmitter is included in a patient monitor that is usually carried by the patient to monitor patient information including, for example, electrocardiogram (EKG), blood pressure, blood oxygen level and temperature. Further, the receiver is typically connected to or is part of a monitoring room or a central station and receives the patient information transmitted by the patient monitor.

In conventional medical telemetry systems, the communication is mostly one-way in an uplink direction (i.e., from the patient monitor to the central station). The transmission signals are received at ceiling-mounted antennas and demodulated at the central station. The patient information is processed at the central station and physiological waveforms are displayed for monitoring the physical status of the patient. In one example, a transmitter in the patient monitor operates with a receiver at the central station on one of a plurality of radio channels where each one of the radio channels operates over a pre-defined carrier frequency. As such, each radio channel is related to one of the pre-defined radio frequency (RF) carrier frequencies. This arrangement is known as frequency division multiple access (FDMA) transmission, and the individual transmission channels in such an arrangement are said to be multiplexed in frequency or simply frequency-multiplexed.

One difficulty associated with an FDMA transmission channel in a hospital setting occurs because of the frequency-selective nature of the indoor radio channel. A typical point-to-point indoor radio link will have a frequency response that varies greatly in amplitude over the 608–614 MHz band. This frequency response changes with the relative position of the transmitter and the receive antennas within the hospital. For the single telemetry radio channel, this phenomenon is called flat fading, and it causes the amplitude and phase of the radio signal to vary with the location of the telemetry unit in the building and also with environmental changes that occur over time. The most commonly employed methods for dealing with fading are increased link margin and antenna diversity. Increasing the link margin means that a higher power level is used in the transmitter than would be predicted to be necessary by theory. Providing multiple receive antennas, located at different points in the building but with overlapping coverage areas, allows the receiver to choose one of a number of different channel responses for a given transmitter. A well-known alternative to antenna diversity is frequency diversity; a frequency-diverse transmission spreads the transmission out in frequency, so that there is a high probability that some sub-band of the transmission passes through the frequency-selective channel in a region of high channel response.

It is desirable to extend existing FDMA medical telemetry systems to accommodate two-way communication between the patient monitors and the central station. A two-way medical telemetry system would use a control channel to transmit control information from the central station to the patient monitors. Such two-way medical telemetry systems could be used, for example, to instruct an individual patient monitor to modify its transmitting frequency or to trigger a reading of the patient's blood pressure.

In one alternative, the control channel can operate on at least one in-band channel, chosen from among the pre-existing FDMA channels provided for telemetry transmissions. For example, in the 608–614 MHz band, the control channel would operate on one channel of bandwidth 25 KHz within the approximately 6 MHz of available bandwidth. This alternative has disadvantages because it limits the number of channels within the 6 MHz bandwidth that are available for transmitting patient data. A further disadvantage is that the receiver, which is part of a wearable patient monitor, cannot make use of antenna diversity for mitigation of fading effects. Furthermore, this alternative has other potential disadvantages associated with interference. With an in-band control channel, it is possible for interference to be caused by the telemetry monitor's own transmission, even though the two transmissions (control data and patient data) are transmitted and received in different FDMA channels within the over-all frequency band. This interference is due to the signal transmitted at the monitor is so much stronger than that received at the monitor. In addition, interference may caused in a patient monitor from adjacent patient monitors that transmit patient data to the central station in bands that are near to the frequency used by the control data transmission.

In another alternative, the control channel operates on an out-of-band channel. For example, in the 608–614 MHz band, the control channel would operate in a band outside the approximately 6 MHz bandwidth. The out-of-band channel control channel could operate on one of the other WMTS bands, for example, 1395–1400 MHz or 1427–1429.5 MHz. In one respect, this alternative is advantageous because the control channel does not operate on one of the channels in the 6 MHz band used to transmit the patient data. However, in another respect, this alternative has several disadvantages. First, the out-of-band control channel operates on a higher frequency than the in-band channels (about 1400 MHz compared to about 600 MHz). As such, separate antennas would be required for the different frequencies in both the central station and the patient monitors. In addition, the propagation characteristics are different for the higher frequency out-of-band control channel, and thus the spacing of the antennas for the out-of-band control channel would be at different intervals than the spacing for the antennas for the in-band channels. Therefore, an out-of-band control channel would increase the cost of the medical telemetry system.

As such, it would be desirable to have a medical telemetry system with the ability of two-way communication of information between the central station and the patient monitor that makes use the same band of frequencies for both telemetry communications and control communications.

Such a system can address the effects of frequency-selective signal fading without the advantage of antenna diversity. Additionally, the system can limit the power of the control transmission, so as to minimize the interference of the control transmission to the telemetry transmission. In addition, it would be desirable to have a medical telemetry system that allowed the use of an in-band control channel that did not operate on a communication channel that could be allocated for communication of patient information. It would also be desirable to have a system that did not require additional antenna configurations and that had the capability of determining and canceling the interference associated with such two-way communication.

BRIEF SUMMARY OF THE INVENTION

In one exemplary embodiment, a medical telemetry system comprises a central station that includes a central station receiver and a central station transmitter. The central station receiver and the central station transmitter operate on a predetermined frequency bandwidth having a plurality of frequency-multiplexed transmission channels, separated from each other in frequency by a plurality of guard bands. Each of the plurality of transmission channels is separated from the adjacent transmission channel by one of the plurality of guard bands. The central station receiver is configured to wirelessly receive patient data from at least one of the plurality of transmission channels. The central station transmitter is configured for wirelessly transmitting control data information via the plurality of guard bands. At least one patient monitor is provided that includes a patient monitor receiver and a patient monitor transmitter that both operate on the predetermined frequency bandwidth. The patient monitor is wirelessly connected to the central station. The patient monitor receiver is configured for wirelessly receiving the control data information from the central station transmitter via at least one of the plurality of guard bands. The patient monitor transmitter is configured for wirelessly transmitting the patient data to the central station receiver via one of the plurality of frequency-multiplexed transmission channels.

DETAILED DESCRIPTION OF THE INVENTION

Figure 1:
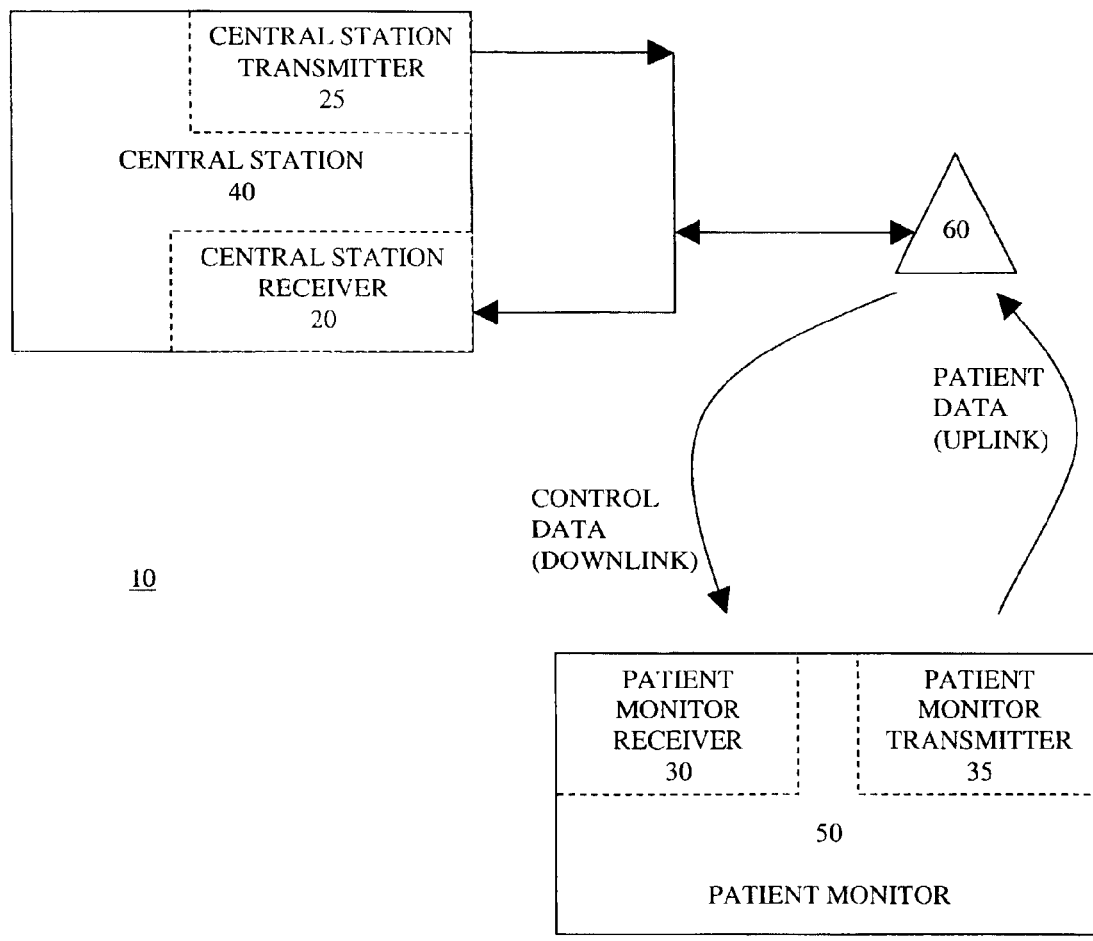
FIG. 1 is a block diagram view of one exemplary embodiment of a medical telemetry system.

In one embodiment as shown in FIG. 1, a medical telemetry system 10 includes a central station 40 that is wirelessly connected to a patient monitor 50 via an antenna node 60. The central station 40 comprises a central station transmitter 25 connected to the antenna node 60 for transmitting control data and/or control messages to the patient monitor 50 (downlink transmission). The central station 40 also comprises a central station receiver 25 connected to the antenna node that receives patient data from the patient monitor 50 (uplink transmission). The patient monitor 50 comprises a patient monitor transmitter 35 that transmits patient data to the central station receiver 20 of the central station 40. The patient monitor 50 also comprises a patient monitor receiver 30 that receives control data from the central station transmitter 25.

In operation, the patient monitor transmitter 35 operates on a predetermined frequency bandwidth that is composed of a plurality of frequency-multiplexed transmission channels and a plurality of guard bands. Guard bands separate each of the transmission channels. The patient monitor transmitter 35 uses one of the transmission channels to transmit the patient data to the central station receiver 20. In one embodiment similar to frequency division multiple access (FDMA) communications, each patient monitor 50 is assigned a specific transmission and/or data channel to transmit its specific patient data, and the central station 40 can identify the particular patient monitor 50 that is transmitting information by identifying the data channel from which the patient data is being received. In one embodiment, the predetermined frequency bandwidth comprises 6 MHz and the number of channels (data channels and guard bands) comprises 240 channels spaced a 25 kHz. In addition, the frequency band can comprise one of the following frequency bands: 608 to 614 MHz, 1395 to 1400 MHz or 1427 to 1429.5 MHz. Further, the central station transmitter 25 transmits control data to the patient monitor receiver 30 using the guard bands in the frequency bandwidth. The central station transmitter 25 transmits control data using each of the guard bands. As such, the central station transmitter 25 broadcasts the control data on each of the guard bands in the frequency band similar to multi-carrier modulation (MCM). This transmission of the control data does not experience flat fading as a single FDMA channel may suffer. Therefore, frequency diversity could be used at the patient monitor receiver 30 to combat signal cancellation due to multipath and obviate the need for a fade margin in the downlink transmission direction. The transmission of the control data is frequency selective in that if complete cancellation of the control data occurs at one specific frequency, there will be other frequencies in the frequency band where cancellation does not occur, and the patient monitor receiver 30 is able to receive the control data on these other frequencies. This technique can be described as a "spread-spectrum overlay" type of channel where the spread-spectrum control data broadcast in the same band as the FDMA patient data transmissions.

Figure 2:
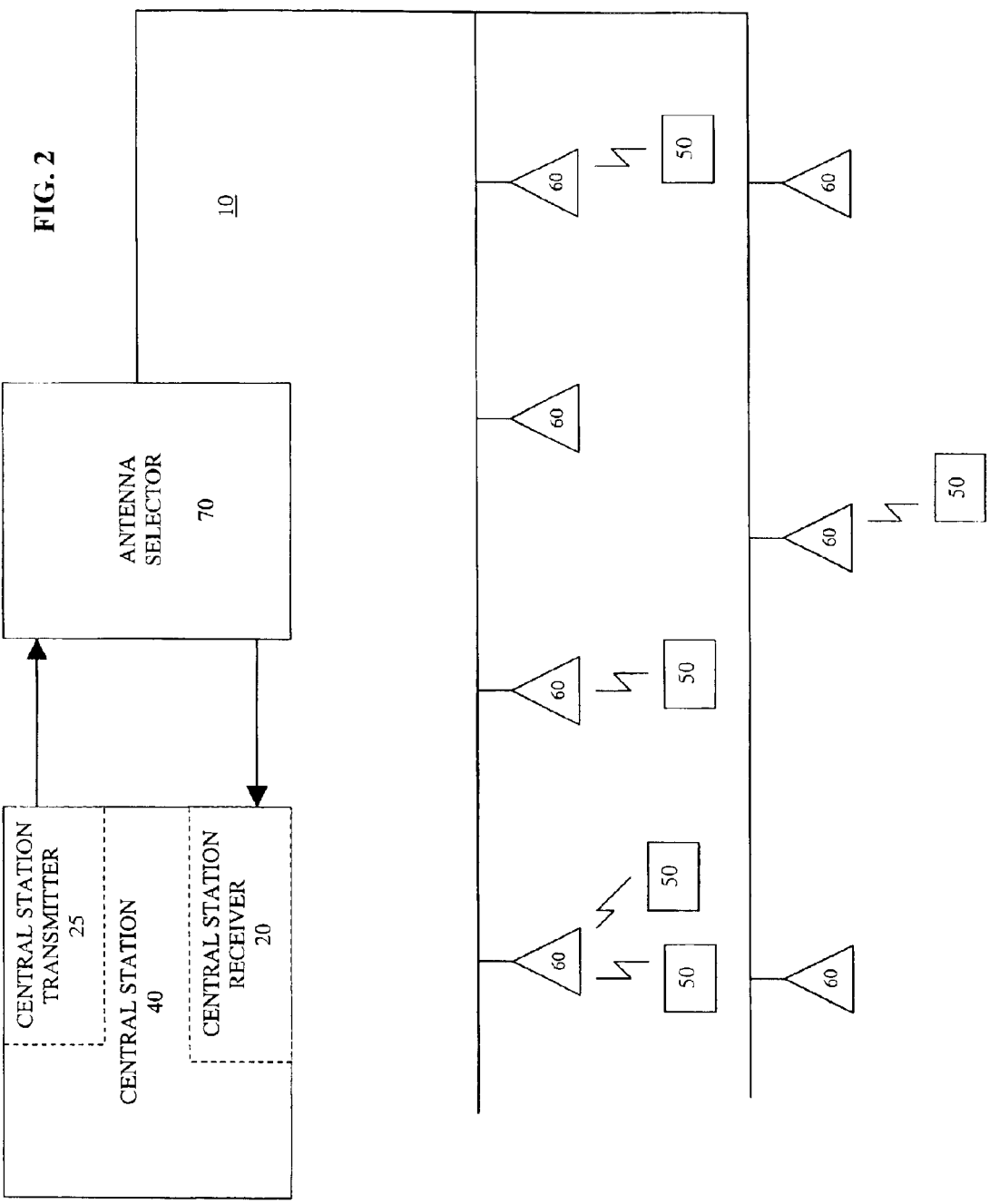
FIG. 2 is a block diagram view of another exemplary embodiment of a medical telemetry system.

In FIG. 2, another embodiment of the medical telemetry system 10 includes a central station 40 comprising a central station transmitter 25 and a central station receiver 20 that are connected to an antenna selector 70. A plurality of antenna nodes 60 is connected to the antenna selector 70. A plurality of patient monitors 50 is wirelessly connected to the central station 40 via the plurality of antenna nodes 60. The plurality of antenna nodes 60 can be configured within a structure, such as a hospital. In addition, since the central station transmitter 25 and the central station receiver 20 operate in the same frequency band, the plurality of antenna nodes 60 can be used to transmit and receive data. This medical telemetry system 10 configuration is advantageous over other systems because it allows the same plurality of antenna nodes 60 to be used for both transmitting and receiving data and, therefore, separate antennas for transmitting data and for receiving data are not required. Similar to FIG. 1, each patient monitor 50 of FIG. 2 includes a patient monitor receiver 30 (FIG. 1) and a patient monitor transmitter 35 (FIG. 1). As discussed above, the central station receiver 20 is configured for wirelessly receiving patient data from the each of the patient monitors 50. In addition, the central station transmitter 25 is configured to transmit control data to each of the patient monitors 50 using the guard bands in the frequency bandwidth.

As discussed above, in order to make use of the entire channel bandwidth (for example, 6 MHz), multi-carrier modulation (MCM) is used to broadcast the control data from central station transmitter 25 via the guard bands to the patient monitors 50. The MCM technique uses multiple narrowband carriers to transmit the control data. In one version of the technique, all the carriers (guard bands) are redundantly modulated with the same message. In addition, a code word can be used to specify different modulations for each carrier to increase throughput.

When using the MCM technique for the in-band control channel, the guard bands are positioned at a set of carrier frequencies that are midway between center frequencies of the data channels. All of these guard bands would be used to transmit the same control data at a symbol rate substantially less than that of the data channels. In one embodiment, the MCM tone bandwidth is about 1 kHz. In addition, the modulation scheme that is used could be one of a number of a number of schemes suitable for radio frequency (RF) transmission, such as binary phase shift keying (BPSK), quadrature phase shift keying (QPSK), orthogonal quadrature phase shift keying (OQPSK) or standard multiple shift keying (MSK). In even another system, QPSK with root-raised-cosine signaling waveforms can be used to minimize the bandwidth of the individual carriers. Additionally, the control data can be received by the patient monitor receiver 30 using any one of the individual carriers. However, in one embodiment, optimal frequency diversity reception can be achieved by combining multiple carriers according to the maximal ratio combining rule. The specific parameters of such a combining rule can be computed from observations of the MCM transmissions at the patient monitor receiver 30.

In another embodiment, rather than using a combining rule computed from the data at the patient monitor receiver 30, the channel is sounded by transmission of known signals, and the channel frequency response is obtained by observation of the channel's effect on these signals. These transmissions do not carry information, but rather are used to determine the frequency response of the channel. In one embodiment, a single tone is transmitted in each of the guardbands, accompanied by a reference tone at some known frequency, such as the center frequency of the first guardband. The two transmitted tones would be equal in both phase and amplitude. From each transmission, the phase and amplitude responses of a single guardband could be obtained, relative to the reference tone, by observation of the relative phase and amplitude of the two tones. The embodiment just described has the disadvantage that a great deal of power must be concentrated into a single guardband, potentially disrupting telemetry channels with similar frequencies. An alternative embodiment that avoids this disadvantage uses the Hadamard transform to structure a sequence of transmissions for channel sounding. The Hadamard transform is used to arrange subsets of the set of guardband tones into a waveform for transmission through the channel. Each transmission has tones arranged to form one of the Hadamard basis vectors, which is composed of 1's and 0's; for each 1, a tone is transmitted, for each zero, no tone is transmitted. When all of the Hadamard basis vectors are present in the observed data set, the observations can be solved for the frequency response of the channel at the set of tone frequencies. In this way, the transmitted energy can be spread throughout the usable band, minimizing interference effects. The solution of a matrix equation with a Hadamard matrix as its coefficient has certain well-understood computational benefits.

As described above with reference to the medical telemetry system 10, the central station transmitter 25, the central station receiver 20, the patient monitor transmitter 35 and the patient monitor receiver 30 operate in the same frequency band. The co-location of these transmitters 25, 35 and receivers 20, 30 on the same two-way link means that the medical telemetry system 10 should have the capability of handling local transmit/receive interference. At the central station the same antenna node 60 is used for both the downlink transmission of control data and received uplink transmission of patient monitor 50. As such, crosstalk will typically be generated at the antenna node 60 from the transmitted control data and the received patient data. Similarly, at the patient monitor 50, the control data is received in the presence of the transmission of patient data by the patient monitor 50. The crosstalk that is found in the medical telemetry system 10 is similar to near-end crosstalk (NeXT) in full-duplex communications, since the uplink and downlink can be specified as being spectrally disjoint, in that the guardbands do not overlap the frequency multiplexed transmission channels.

One embodiment of the patient monitor receiver 30, an analog comb filter is provided at the input of the patient monitor receiver 30 to block the contents of the frequency multiplexed telemetry data transmission channels. The passbands of the comb filter are centered on the guardband center frequencies, and the stopbands are centered on the telemetry data center frequencies.

In one embodiment, the crosstalk can be reduced or eliminated by subtracting an adaptively filtered version of the transmission from the reception. This method of subtracting the signal can especially be used in the control station receiver 20 and the patient monitor receiver 30.

With reference to the central station receiver 20 and the patient monitor receiver 30, signal processing can be implemented in the respective receiver 20, 30 to subtract the adaptively filtered version of the transmitted signal from the received signal. To determine the requirements for rejecting crosstalk interference at both ends, the uplink and downlink link budgets are estimated.

With reference to the uplink transmission (from the patient monitor transmitter 35 to the central station receiver 20), the link budget can be estimated. In one embodiment, where the central station receiver 20 has a receiver temperature of 290K, a receiver bandwidth of 25 kHz, and a noise figure of 7 dB, a receiver noise power of −153 dBW can be determined with reference to the input. Further, if the signal to noise ratio (Eb/N0) required to support the desired bit error rate is 13 dB and the data rate is 10 kBits/sec, a signal-to-noise power ratio of 9.1 dB would yield an uplink receive power of −143.9 dBW. The free-space path loss at a range of 20 meters (coverage edge) and a frequency of 610 MHz is determined to be about 54 dB, therefore, with a transmit power of about −62 dBW, the transmit power margin is calculated to be about 27.9 dB. It should be appreciated that this transmit power margin includes propagation through at least one interior wall in addition to fade margin, and therefore the fade margin is in the range of about 20 and 25 dB.

For the downlink transmission (from the central station transmitter 25 to the patient monitor receiver 30), the link budget can be determined for the multitone modulation transmission of the control data. In one embodiment, where the patient monitor receiver 30 has a temperature of 290K, a receiver noise bandwidth of 2 Nc kHz (Nc is the number of narrowband carriers used in the multi-carrier scheme) and a receiver noise about 12 dB, a noise power of about (−159+10 log(Nc)) dBW is determined with reference to the input. If the value of Eb/N0 required to obtain the desired bit error rate is 13 dB and the data rate is 1 kBit/sec, the signal-to-noise power ratio is calculated as about (10−10 log(Nc)) dB. As such, a minimum receive power of −149 dBW is determined. For a maximal path loss of 54 dB, a 6 dB interior-wall margin and no fade margin, the total transmitted downlink power would be −89 dBW. Therefore, the power per carrier is (−89−10 log(Nc)) dBW. Since the minimum receive power for the uplink is −144 dBW, the downlink power in a single carrier is at most (55−10 log(Nc)) dB above the minimum receive power.

Figure 3:
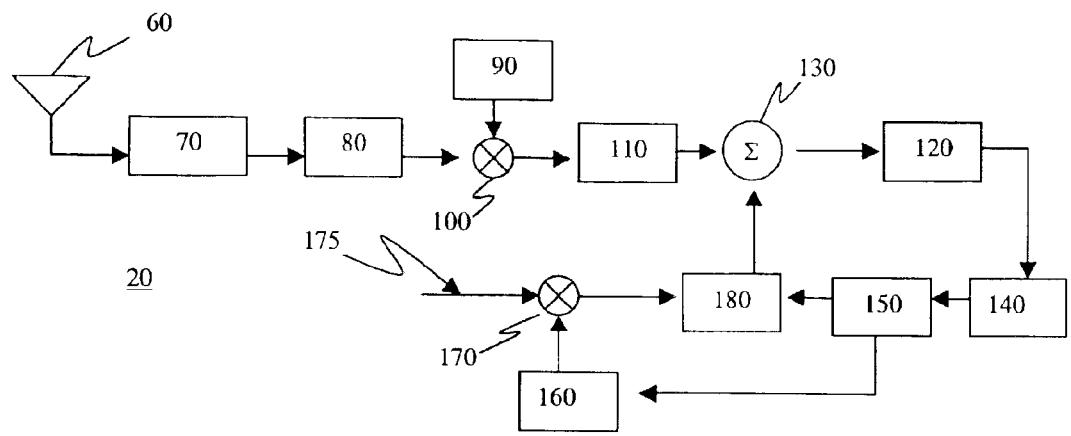
FIG. 3 is a block diagram view of one exemplary embodiment of a central station receiver.

Typically, the relative power of the single carrier and the received uplink signal is the quantity of interest at the central station receiver 20. Only the multitone modulation carriers in the adjacent guardband(s) will interfere with the received uplink signal at the central station receiver 20. The FDO carriers others will be rejected by a selection filter (FIG. 3). In one embodiment, if 32 carriers are used, the power of the interfering single-carrier downlink signal would be 40 dB up from the minimum uplink receive power. Further, if 32 carriers are used, about every 8th guard band would contain a carrier. In another embodiment, if 120 carriers are used, every other guard band would contain a carrier, and every frequency division multiple (FDM) channel would be adjacent to one FDO carrier. In this case, each carrier would be about 34 dB up from the minimum required receive power. At the patient monitor 50, with a minimum received power of −149 dBW and a transmitted power of −62 dBW, the transmission is 87 dB up from the minimum receive power.

With respect to the central station receiver 20, in one embodiment, each of the uplink FDM channels is separated by 25 kHz. In operation, the central station receiver 20 includes signal processing that selects a single FDM channel. Any out-of-band energy is filtered out. The filtered signal is converted to a complex baseband signal. In this example, any interference introduced by the downlink transmission from the central station transmitter 25 will consist of one or two narrowband carriers that are situated at 12.5 kHz from the center of the desired FDM band. Each carrier signal will exceed the desired signal in average power by at most (55−10 log(Nc)) dB as determined hereinabove.

It should be understood that the interference power determined hereinabove above is the power from a single antenna node 60 (FIG. 1). If a plurality of antenna nodes 60 (FIG. 2) is connected to a central station receiver 20, as shown in FIG. 2, the multiple versions of the interference will combine at random delays to form a frequency-dependent interference. At some frequencies, this interference could be significantly higher than the various signal power determined hereinabove. Unlike the linear filter characteristic of the RF channel, this distribution of interference power typically will not change with time, since it can depend on the cable lengths to the plurality of antenna nodes 60 (FIG. 2).

In one embodiment, as shown in FIG. 3, the central station receiver 20 of the central station 40 comprises an antenna selector 70 that is connected to the plurality of antenna nodes 60. The antenna selector 70 selects one of the plurality of antenna nodes 60 to receive the patient data being transmitted by the patient monitor 50. An attenuator 80 is optionally connected to the antenna selector 70 to attenuate the received signals. A first intermediate frequency (IF) mixer 100 is connected to the attenuator 80 and a synthesizer 90. A bandpass filter 110 is connected to the output of the first IF mixer 100. The output from the bandpass filter 110 is provided to a baseband mixer/converter 120 via a summer 130. An analog to digital converter (ADC) 140 is connected to the output of the baseband mixer/converter 120 for converting the analog complex baseband signal to a digital signal. A digital signal processor (DSP) 150 is connected to the output of the ADC 140. A digitally controlled synthesizer 160 is coupled to the DSP 150 and a second IF mixer 170. The DSP 150 supplies control information to the synthesizer 160, and the synthesizer 160 outputs an analog waveform to the second IF mixer 170. A variable phase shifter and attenuator 180 is connected between the second IF mixer 170 and the summer 130. The variable phase shifter and attenuator 180 is controlled by digital input from the DSP 150.

As further shown in FIG. 3, the signal processing of the received patient data includes bandpass filter 110 after the IF mixer 100 and before the baseband mixer/converter 120. The conversion to complex baseband in the central station receiver 20 may also optionally involve hard limiting of the received patient data signal at the output of the baseband mixer/converter 120. It is important that the interfering signal be attenuated to a level equal to or below the desired signal level prior to the conversion if such a nonlinearity exists. This attenuation can be accomplished by decreasing the width of the passband of the bandpass filter 110 at the output of the first IF mixer 100. For example, if the interfering signal is at least 35 dB up from the desired signal, an attenuation of the interfering signal by more than 45 dB at the bandpass filter 110 would be desired before the limiter nonlinearity. In another example, the baseband mixer/converter 120 can be operated in a linear mode, and the input to the baseband mixer/converter 120 can be adjusted to make full use of the dynamic range the ADC 140. Further in this example, if the bandpass filter 110 attenuated the interfering signal 15 dB, the interfering signal would be about 20 dB up from the desired signal. Using the full dynamic range of the ADC 140, the interfering signal could be suppressed to −60 dB with respect to the desired signal by an initial digital low pass filter in the baseband processing. As a result, the residual desired signal would have sufficient dynamic range for demodulation.

In another embodiment, as shown in FIG. 3, the interference signal can consists of a transmitted message that is known exactly to the central station receiver 20, adaptive cancellation of the interference can be accomplished. To perform adaptive cancellation, the analog baseband downlink transmission is modulated to the IF used in the central station receiver 20. This modulated version of the baseband downlink signal is input 175 to the second IF mixer 170 as shown in FIG. 3. If the input 175 is modulated to the frequency it occupies in the IF signal, and if the phase and amplitude are matched, the modulated version of the baseband downlink signal can be subtracted from the received signal at the central station receiver 20. With reference to the modulated version of the baseband downlink signal, the phase and amplitude are typically not known because these values are determined by unknown factors, such as the length of the cable connecting the antenna node 60 to the central station receiver 20. In a medical telemetry system 20 with a plurality of antenna nodes 60, the phase and amplitude can be determined by a random combination of interference from multiple antennas. The exact frequency, phase and amplitude of the modulated version of the baseband downlink signal would be controlled by the DSP 150 that adjusts the phase and amplitude response of the variable phase shifter and attenuator 180 to reduce the interference observed in the received signal, which is computed by the DSP 150.

With reference to the patient monitor 50 and the link budget determined hereinabove, the uplink transmit power at the patient monitor 50 is about 87 dB up from the minimum receive power. However, as described above, the received signal (control data) is transmitted using each of the guard bands and is, therefore, spread all over the entire frequency band, for example 6 MHz. In addition, the patient monitor 50 transmits the transmitted signal (patient data) over, for example, a 25 kHz sub-band at a known frequency. Similar to the central station receiver 20, a source of interference for the patient monitor receiver 30 is the transmitted signal (patient data) transmitted by the patient monitor 50, itself, since the transmitted signal is transmitted in the same frequency band as the received signal (control data). In order to reject the transmitted signal, the patient monitor receiver 30 filters the IF signal to reject the known frequency of the transmitted signal interference.

Figure 4:
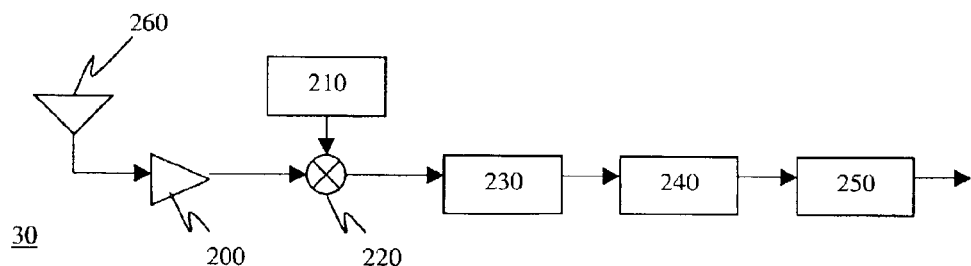
FIG. 4 is a block diagram view of one exemplary embodiment of a patient monitor receiver.

As shown in FIG. 4, one embodiment of the patient monitor receiver 30 comprises antenna 260. The antenna 260 is connected to an amplifier 200 for amplifying the received signal. The amplifier 200 is connected to IF mixer 220. A synthesizer 210 is also connected to the IF mixer 220. A bandpass filter (BPF) 230 is connected to the IF mixer 220. An interference reject filter 240 is connected to the BPF 230 and rejects a predetermined frequency of the received signal. A baseband mixer 250 is connected to the interference reject filter 240. To reject the transmitted signal (patient data) from the received signal (control data), the stopband of the interference reject filter 240 can be as wide as required to reject the interference. In one embodiment, the interference reject filter 240 can comprise a parallel combination of bandpass filters. It should also be appreciated that the power spectral density (PSD) of the transmitted signal can fall to −90 dB with respect to its peak at a frequency interval of about 16 kHz. It should further be noted that if the interference reject filter 240 rejects a substantial portion of the input band, the downlink link budget should be adjusted to compensate by increasing the transmitted power. The power in the frequency band that remains after filtering should meet the minimum receive power determined hereinabove at worst-case (max range) conditions.

In addition, other, near-by patient monitors 50 can cause interference at the patient monitor receiver 30. The frequency of the interference caused by the other, near-by patient monitors 50 is typically not know by all the patient monitors 50. However, it will be centered at one of the center frequencies of one of the frequency-multiplexed telemetry radio channels, and so it may be at least substantially attenuated, if not eliminated, by the aforementioned bank of bandpass filters. Additionally, since the frequency of the interference is not known, the interference can be at least partially suppressed by an adaptive scheme. In one embodiment, the patient monitor receiver 30 can further comprise a bank of bandstop filters (not shown) that could be switched in and out. While the interference from a near-by patient monitor 50 may not be received at as high a power as the locally transmitted signal interference, the interference from the near-by patient monitor 50 could be as much as 70 dB up from the minimum received signal power.

Given this interference power, a substantial portion of the frequency-selective rejection should to be done before the received signal is digitized.

The patient monitor receiver 30 can further be adapted to receive baseband multi-carrier modulation signals. In one embodiment, to perform this function, the patient monitor receiver 30 can further include or be adapted to perform (via a digital signal processor) a fast fourier transform (FFT) to separate the received signal into frequency bins. In another embodiment to perform these functions, a bank of filters 350 (FIG. 5) can be used at the input signal. In order to obtain the optimal signal-to-noise ratio, the component carriers of the multi-carrier signal can be combined using the well-known technique of maximal ratio combining. Using maximal ratio combining scheme, the channel frequency response is estimated at each of the component carrier frequencies and the observed signals are weighted by the conjugates of these estimated responses.

Figure 5:
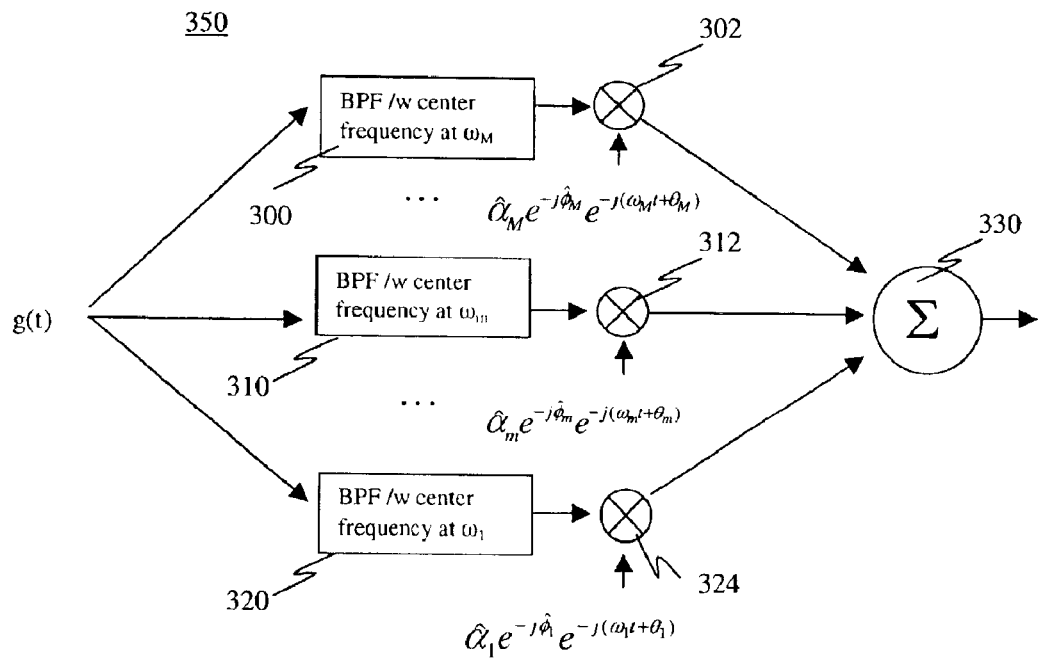
FIG. 5 is a block diagram view of one exemplary embodiment of a front end to a patient monitor receiver.

As shown in FIG. 5, the input signal g(t) is the sampled, complex baseband signal associated with the bandpass transmission, and is given by:

$$g(t) = \sum_{m=1}^{M} s(t) e^{j(\omega_m t + \theta_m)} \alpha(\omega_m) e^{j\phi(\omega_m)} + n(t) \tag{1}$$

where s(t) is the complex baseband modulated waveform, consisting of a sequence of the basic pulse waveforms used, according to the modulation scheme, to encode the data, and $\omega_m$ is the frequency of the $m^{th}$ component carrier, and $\theta_m$ is its phase relative to a reference clock of the patient monitor receiver 50. The factor $\alpha(\omega_m)$ is the amplitude response of the channel at the frequency of the $m^{th}$ carrier, and the quantity $\phi(\omega_m)$ is the phase response at that frequency. The frequency response of the channel changes slowly with time. The n(t) term is additive noise and can be at least as wideband as the sum of the carrier-modulated baseband signals. The multi-carrier modulation signal, as modified by the frequency response of the channel, is expressed in Equation (1).

In FIG. 5, each of the bandpass filters (BPF) 300, 310 and 320 are used to select one each of the terms of the sum in Equation (1). Multipliers 302, 312 and 324 are connected respectively to the BPF 300, 310 and 320 to perform multiplication and both frequency translation to zero frequency for each carrier and the complex weighting required for maximal-ratio combining. The output of the multipliers 302, 312 and 324 are connected to summer 330. In one embodiment as shown in FIG. 5, the channel frequency response is known and also supplied to the multipliers 302, 312 and 324. In another embodiment, the channel frequency response is estimated. In this estimation, an average value of each of the outputs of the bandpass filters is formed and translated to zero frequency with the phase of the modulating (message) information removed. This modulating information can either be known, as in a training sequence, or the patient monitor receiver 30 can perform a decision-directed operation where the patient monitor receiver 30 uses local decisions to remove modulating information from the observation. In yet another embodiment, the channel frequency response is known due to sounding of the channel, which is done by transmitting a known set of test signals through the channel so that the patient monitor receiver 30 can deduce the channel frequency response from the received waveforms. In one embodiment, such known signals can comprise a set of individual tones at the guardband center frequencies. In another embodiment, such known signals can comprise a set of multi-tone transmissions, structured with reference to the basis vectors of the Hadamard transform; the received values from these transmissions can be used to form a set of simultaneous, linear equations at the patient monitor receiver 30, the coefficients of which are given by the Hadamard basis vectors. Such a set of equations can be solved by various techniques to derive the required set of channel frequency responses.

It should be appreciated that the band of filters 350 in FIG. 5 are not a complete baseband receiver, but only the maximal ratio combiner front-end to such a baseband receiver. In order to complete the demodulation, the baseband output of the summer 330 will undergo matched filtering timing recovery and carrier recovery. In one embodiment, band of filters 350 of FIG. 5 comprise multi-rate digital filters.

Figure 6:
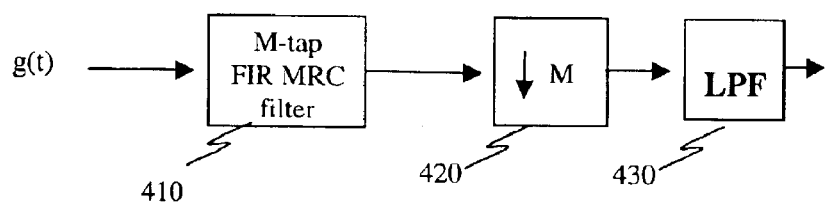
FIG. 6 is a block diagram view of another exemplary embodiment of a patient monitor receiver.

In another embodiment, the patient monitor receiver 30 can also perform maximal ratio combining (MRC) by applying the required weights to each carrier by filtering the input signal. As shown in FIG. 6, if the filter 410 applies the correct weight at the frequency of each FDO carrier, maximal ratio combining can be achieved by the decimation. It should appreciated that maximal ratio combining is performed in order that the aliased carriers add in-phase. If the phase response of the channel were constant, the aliasing step would result in all the carriers adding up in phase. If the amplitude response were also constant for all frequencies, the signal to noise ratio (SNR) of the sum of the signals would be the same as that of the components of the signal. However, typically, the channel has a non-constant frequency response and so the carriers will not naturally add in-phase and the SNR of the sum will be less than that of a well-constructed weighted sum. Therefore, correction of the phase and amplitude associated with maximal ratio combining should be applied prior to the decimation step using decimator 420.

Once the maximal ratio combining and co-phasing weights are applied to the observation by the FIR filter 410, the output is decimated by a factor of M (the number of carriers) using decimator 420. After decimation, a lowpass filter (LFP) 430 filters the decimated signal to remove the interference caused by the data channels. Although all the carriers are aliased to zero frequency, any residual energy from the frequency-multiplexed telemetry signals are aliased to non-zero frequencies and can be eliminated by digital filtering given a long enough observation and high enough dynamic range. In one embodiment, the filter 410 has a real-valued impulse responses. The initial M-tap MRC filter 410 will produce one output value for every M input values. These output values will be sampled at a rate that is much higher than the sample rate, in general.

The FIR filter 410 can be designed to perform maximal ratio combining given a knowledge of the channel frequency response at the carrier frequencies as follows:

We will define $\alpha=[\alpha_1 e^{-j\phi_1} \ldots \alpha_M e^{-j\phi_M}]$ to be the MRC weights in the frequency domain, and the associated component carrier frequencies at baseband are:

$$\omega_i = \begin{cases} (i-1)\frac{2\pi}{T_s M} & \text{for } 1 \leq i < \frac{M}{2} \\ (i-M-1)\frac{2\pi}{T_s M} & \text{for } \frac{M}{2} \leq i \leq M \end{cases} \quad (2)$$

where $T_s$ is the sampling period. It should be appreciated that the inverse of $T_s M$ is the frequency separation of the component carriers in Hertz (Hz)

Further, the FIR tap weights are set to be equal to:

$$h_k = \frac{1}{M} \sum_{m=1}^{M} \alpha_m e^{-j\phi_m} e^{j(m-1)\frac{2\pi k}{M}} \text{ for } k = 0, \ldots, (M-1) \quad (3)$$

These are the inverse discrete Fourier transform (IDFT) coefficients of the desired MRC weights. In this case, the discrete-time Fourier transform (DTFT) domain frequency response of the MRC filter can be expressed as:

$$H(e^{j\omega}) = \sum_{k=0}^{M-1} h_k e^{-j\omega k T_s} \text{ for } -\frac{\pi}{T_s} \leq \omega \leq \frac{\pi}{T_s} \quad (4)$$

$$= \sum_{k=0}^{M-1} \frac{1}{M} \sum_{m=1}^{M} \alpha_m e^{-j\phi_m} e^{j(m-1)\frac{2\pi k}{M}} e^{-j\omega T_s}$$

$$= \sum_{m=1}^{M} \alpha_m e^{-j\phi_m} \frac{1}{M} \sum_{k=0}^{M-1} e^{j[(m-1)\frac{2\pi}{M} - \omega T_s]k}$$

This means that $$H(e^{j\omega_i}) = \alpha_i e^{-j\phi_i} \text{ for } i=1, \ldots, M \quad (5)$$

as required for maximal ratio combining, since the factor $$\sum_{k=0}^{M-1} e^{j[(m-1)\frac{2\pi}{M} - (i-1)\frac{2\pi T_s}{T_s M}]k} = \sum_{k=0}^{M-1} e^{j(m-i)\frac{2\pi k}{M}} \quad (6)$$

$$= \begin{cases} M & \text{if } m = i \\ 0 & \text{otherwise} \end{cases}$$

It is should be appreciated that the FIR filter 410 delivers the desired weights at the frequencies described by equation (2). If the local oscillator (LO) on the patient monitor receiver 20 side is not at the correct frequency with respect to the modulation at the patient monitor transmitter 25, the carriers will not be at these frequencies, but rather at some near-by ones. Since the frequency response of the MRC filter at frequencies between those of equation (2) are simply interpolated values, if the frequency mismatch is small, relative to the spacing between carriers, the applied weight will be close to correct. The LO frequency mismatch can be estimated from the final, timing-recovered data sequence, and the result can be sent to an external, digitally controlled synthesizer so as to line the carriers up with the frequencies of equation (2).

Further, the FIR tap weights $\{h_k\}$ can be estimated from the observed data. The input signal will be described as in equation (1), but the sampling of g(t) will be explicit, in that the $k^{th}$ sample occurs at the time $(kT_s+\tau)$:

$$g(k) = s(kT_s + \tau) \sum_{m=1}^{M} \alpha_m e^{j\phi_m} e^{j[\omega_m(kT_s+\tau)+\theta_m]} + \tilde{n}(k) \quad (7)$$

where $\alpha(\omega_m)$ has been shortened to $\alpha_m$, and $\phi(\omega_m)$ to $\phi_m$, to be consistent with the definition of $\alpha$. Further, the symbol for the noise in equation (7) has been changed to distinguish the continuous noise of equation (1) from the noise samples of equation (7). The sampling phase, $\tau$, accounts for the fact that the ADC 510 (FIG. 7) at the patient monitor receiver 20 side is not synchronized with the symbol clock at the central station transmitter 25, and note that $0 \leq \tau \leq T_s$.

In addition, g(k) is decimated by M, retaining the $v^{th}$ phase of the decimation. The index of new sequence, l, is defined by the expression k=lM+v, so that $$g_v(l) = s(lMT_s + vT_s + \tau) \times \sum_{m=1}^{M} \alpha_m e^{j[\phi_m + \theta_m + \omega_m \tau]} e^{j\omega_m(lMT_s+vT_s)} + n'(l) \quad (8)$$

This expression gives the decimated signal as the product of the sequence of baseband modulated pulses times a weighted sum of complex carriers plus noise. The weights the carriers are composed of four terms. The first, $\alpha_m'$, is the amplitude of the channel impulse response at the original carrier frequency, the second, $\exp[j\phi_m]$ is a complex exponential of the channel phase response at the carrier frequency, the third, $\exp[j\theta_m]$, is the phase of the $m^{th}$ carrier itself and the fourth, $\exp[j\omega_m\tau]$, is the phase effect of the random phase between the sample clock and the symbol clock for the $m^{th}$ carrier. Now if the inverse DFT of the required MRC frequency domain weights is written, the expression can be shown as:

$$h_k = \frac{1}{M}\sum_{m=1}^{M} \alpha_m e^{-j[\phi_m+\theta_m+\omega_m\tau]} e^{j(m-1)\frac{2\pi k}{M}} \text{ for } k = 0, \ldots, (M-1) \quad (9)$$

then the vector $h=[h_0 \ldots h_{M-1}]$ gives the tap weights that are to be implemented in the filter 410, as shown above. (Compare equation (9) to equation (3).) These weights include compensation for the effects of the random timing phase, $\tau$, in addition to compensation for the linear filter effect of the channel and the random phases of the individual subcarriers.

Using the definition of the carrier frequencies given in equation (2) and the fact that $e^{j2\pi pq}=1$ for integers p and q, the expression can be written as:

$$e^{j\omega_m(lMT_s+vT_s)} = \begin{cases} e^{j\frac{2\pi(m-1)}{T_sM}(lMT_s+vT_s)} & \text{for } 1 \le m < \frac{M}{2} \\ e^{j\frac{2\pi(m-M-1)}{T_sM}(lMT_s+vT_s)} & \text{for } \frac{M}{2} \le m \le M \end{cases} \quad (10)$$

$$= e^{j\left(\frac{2\pi(m-1)v}{M}\right)} \text{ for } 1 \le m \le M$$

Substituting equation (10) into equation (8) and using the definition in equation (9), the following expression is shown:

$$g_v(l) = s(lMT_s + vT_s + \tau)\sum_{m=1}^{M} \alpha_m e^{j[\phi_m+\theta_m+\omega_m\tau]} e^{j(m-1)\frac{2\pi v}{M}} + n'(l) \quad (11)$$

$$= M h_{M-v}^* s(lMT_s + vT_s + \tau) + n'(l)$$

where v can take any value between 0 and M-1, inclusive.

The definition of s(t) (the sequence of baseband modulated pulses) can be shown as:

$$s(t) = \sum_{n=-\infty}^{\infty} b_n p(t - (n-1)T_b) \quad (12)$$

where $b_n$ is the $n^{th}$ data symbol (which may be more than a single bit), p(t) is the signaling waveform, and $T_b$ is the symbol interval. If this definition is substituted in equation (11), the following expression can be shown:

$$g_v(l) = M h_{M-v}^* \sum_{n=-\infty}^{\infty} b_n p(lMT_s + vT_s + \tau - (n-1)T_n) + n'(l) \quad (13)$$

The expression in equation 13 shows that if the patient monitor receiver 30 knows the values of the transmitted bits, and knows the timing phase of the received signal (expressed by $\tau-(n-1)T_n$), then the MRC FIR tap weights can be recovered from the decimated input sequence directly. This recovery need only use a suitable noise reduction technique such as a simple average. The $v^{th}$ phase of the decimated input yields the (M-v)th tap weight of the FIR filter.

Figure 7:
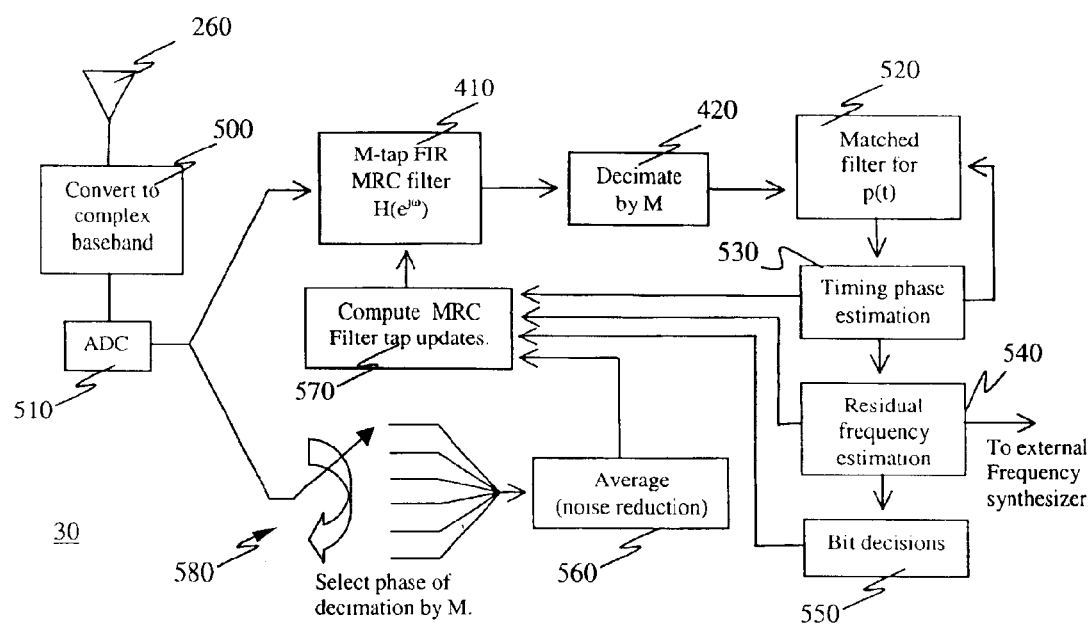
FIG. 7 is a block diagram view of even another exemplary embodiment of a patient monitor receiver.

In FIG. 7, one embodiment of the patient monitor receiver 20 provides an RF observation from the antenna 260 that is converted to analog, complex baseband by, for example, first translating to an IF using baseband converter 500. This complex baseband signal is digitized using ADC 510 at a sample rate adequate to capture the entire channel bandwidth. In one embodiment, the sample rate comprises 6 M samples per second (SPS). The digitized signal is filtered by the FIR maximal ratio combiner (MRC) filter 410 and then decimated by decimator 420 to produce a single signal with maximal SNR. The input to the filter 410 is at the full digitized rate, but the output is at a rate decimated by the number of taps in the filter, so that each input sample causes only a single complex multiplication. The decimated output of the MRC filter is then matched-filtered at filter 520 using the baseband signaling waveform of the individual subcarrier channel. The output of the matched filter 520 is provided to a timing phase estimator 530. Since timing phase estimation methods use only a small number of samples per symbol period, the matched filter 520 typically represents a further stage of decimation.

In one embodiment, the matched filter 520 can comprise a polyphase filter whose phase is controlled by the timing phase estimate. This control is shown as an expression for the undecimated output of the MRC filter 410, assuming that the tap weights are exactly as required for maximal ratio combining. The expression is similar to equation (7) with the MRC weights applied to each subcarrier $$g_{MRC}(k) = s(kT_s + \tau)\sum_{m=1}^{M} \alpha_m^2 e^{j\omega_m kT_s} + n''(k) \quad (14)$$

where the notation for the noise has been changed to reflect the fact that it has been filtered by the MRC filter 410. After decimation by M, with the decimation phase arbitrarily set to zero, the input to the filter 520 as:

$$\hat{g}_{MRC}(l) = s(lMT_s + \tau)\sum_{m=1}^{M} \alpha_m^2 + n''(lM) \quad (15)$$

which is just a scaled version of the sequence of modulated baseband signaling waveforms observed in (filtered) noise. The samples of equation (15) are at some arbitrary phase with respect to the symbol clock of the central station transmitter 25. As such, the matched filter 520 can be a polyphase version of p(t), sampled at a rate higher by some appropriate factor than the sample rate of equation (15). The particular phase of the matched filter 520 used for generation of output samples should be determined by the timing phase estimate, which accounts both for $\tau$ and for the phase of the decimation.

As further shown in FIG. 7, after matched filtering using filter 520 and time phase estimating, the residual modulation frequency is estimated by a residual frequency estimator 540. The input to the residual frequency estimator 540 is a sequence of complex samples sampled at the symbol rate and representing matched filter outputs at the timing phase. These samples all have the same (optimal) SNR. If the local oscillator is not operating at the correct frequency, the center frequency of each subcarrier will be in error by the same offset, say $\Delta\omega$. This offset frequency will cause a phase rotation of the matched filter output of equation (15) and can be estimated. The estimate can be used to control an external digitally controlled oscillator that adjusts the LO frequency with the objective of reducing the rate of phase rotation to zero at the frequency estimator. The phase rotation due to local oscillator (LO) mismatch will also appear in the decimated signal used to estimate the MRC filter coefficients, and the estimated residual frequency can be applied to that computation to increase its accuracy. The estimated residual frequency can also be used to correct the phase of the input samples prior to making symbol decisions.

Bit or symbol decisions are made using decision module 550 on the high-SNR. Frequency corrected samples are fed to a processor 570 that estimates the MRC filter coefficients. This estimation is done on the basis of the decimated signal expressed by equation (13). The effect of residual modulation frequency $\Delta\omega$ is just to multiply $g_v(l)$ by $\exp[j\Delta\omega(1MT_s+vT_s+\tau)]$. Given a knowledge of M, v and n, and given estimates of $\tau$ and $\Delta\omega$, and a good representation of the pulse shape p(t), the $\{h_v\}$ can be estimated from equation (13). In addition the signal from the ADC 510 is provided to a selection module 580 to select the phase of the decimation by M. The output of the selection module 580 is provided to an averaging module 560 to provide average noise reduction to the processor 570 used to compute the MCR filter tap updates.

The operation count of the patient monitor receiver 30 is dominated by the computation involved in the MRC filter 410. Such use is not unexpected, since that the MRC filter 410 has input at the full sample rate while all the other components have inputs at reduced rates. It will be important that in the patient monitor receiver 30 this initial filtering operation be set up as a low-overhead loop. In one embodiment, instructions are counted for an interrupt-driven parallel data transfer.

It should be appreciated that the incoming signal is decimated prior to estimating the taps of the MRC filter 410. This decimation is done for reasons of reducing the computational burden. In fact there is a trade-off that can be made between adaptation rate and required computation, so that the rate of adaptation of the MRC filter 410 can be matched to the Doppler spread on the channel.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A medical telemetry system comprising:
a central station comprising a central station receiver and a central station transmitter, the central station receiver and the central station transmitter operating on a predetermined frequency bandwidth having a plurality of frequency-multiplexed transmission channels and a plurality of guard bands, each of the plurality of frequency-multiplexed transmission channels being separated in frequency by one of the plurality of guard bands, the central station transmitter being configured for wirelessly receiving patient data from at least one of the plurality of frequency-multiplexed transmission channels, the central station transmitter being configured for wirelessly transmitting control data information via the plurality of guard bands; and
a patient monitor comprising a patient monitor receiver and a patient monitor transmitter operating on the predetermined frequency bandwidth, the patient monitor wirelessly connected to the central station, the patient monitor receiver being configured for wirelessly receiving the control data information from the central station transmitter via at least one of the plurality of guard bands, the patient monitor transmitter being configured for wirelessly transmitting the patient data to the central station receiver via at least one of the plurality of frequency-multiplexed transmission channels.

2. The system of claim 1, wherein the central station transmitter of the central station transmits the control data information via the plurality of guard bands using multicarrier modulation (MCM).

3. The system of claim 1, wherein a range of the predetermined frequency bandwidth is selected from the group consisting of 608 to 614 MHz, 1395 to 1400 MHz and 1427 to MHz.

4. The system of claim 1, wherein the predetermined frequency bandwidth comprises about 6 MHz.

5. The system of claim 1, wherein the plurality of frequency-multiplexed transmission channels and the plurality of guard bands comprises 240 channels.

6. The system of claim 1, wherein each of the plurality of frequency-multiplexed transmission channels is spaced about 25 kHz from each other.

7. The system of claim 1, wherein one of the plurality of guard bands comprises a frequency bandwidth of about 25 kHz.

8. The system of claim 1, wherein the central station receiver and central station transmitter are connected to an antenna node for wirelessly transmitting the control data information to the patient monitor receiver and wirelessly receiving patient data from the patient monitor transmitter.

9. The system of claim 1, wherein the central station is connected to a plurality of antenna nodes.

10. The system of claim 1, wherein the central station receiver is configured to use adaptive cancellation for canceling interference caused by the central station transmitter wherein the interference comprises control data being transmitted by the central station transmitter to the patient monitor receiver.

11. The system of claim 1, wherein the patient monitor comprises a plurality of patient monitors and wherein each of the plurality of patient monitors comprise a patient monitor receiver and a patient monitor transmitter.

12. The system of claim 1, wherein the patient monitor receiver is configured to use adaptive cancellation for canceling interference caused by the patient monitor transmitter wherein the interference comprises patient data being transmitted by the patient monitor transmitter to the patient monitor receiver.

13. The system of claim 12, wherein the patient monitor receiver further comprises a filter for filtering interference wherein the interference comprises patient data information being transmitted by others of the plurality of patient monitors.

14. The system of claim 10 wherein the central station receiver comprises:
an antenna selector connected to each of the plurality of antennas for selecting an antenna node for receiving the patient data;
a first IF mixer connected to the attenuator for processing the output from the antenna node and the synthesizer and generating an IF mixer output;
a synthesizer connected to the IF mixer;
a bandpass filter connected to the IF mixer;
a baseband mixer connected to the IF mixer to receive the IF mixer output;
an analog to digital converter (ADC) connected to the bandpass filter;
a digital signal processor (DSP) connected to the ADC;
a digitally controlled synthesizer coupled to the ADC and DSP;
a second IF mixer connected to the digitally controlled synthesizer for combining the output from the digitally controlled synthesizer and a baseband signal;
a variable phase shifter connected to the second IF mixer and the DSP; and
a summer connected between the bandpass filter, baseband mixer and the variable phase shifter.

15. The system of claim 14, wherein the central station receiver further comprises an attenuator connected to the antenna selector for attenuating a received signal to a desired level as an output.

16. The system of claim 1, wherein the patient monitor receiver comprises:
an antenna wirelessly connected to the patient monitor receiver for receiving the control data information via at least one of the plurality of guard bands from the central station transmitter;
an amplifier connected to the antenna for amplifying the received control data information;
an IF mixer connected to the amplifier to generate a IF signal;
a synthesizer connected to the IF mixer;
a bandpass filter connected to the IF mixer;
an interference reject filter connected to the bandpass filter for rejecting a known frequency of an interference signal; and
a baseband mixer connected to the interference reject filter for generating a complex baseband signal for processing by the patient monitor.

17. The system of claim 1 wherein the patient monitor receiver comprises a maximal ratio combining filter for estimating a channel frequency response for each of the guard bands and weighting conjugates of the estimated channel frequency responses such that the control data received via each of the guard bands can be combined into a signal control data signal by the patient monitor receiver.

18. The system of claim 17 wherein the estimation of the channel frequency response uses a Hadamard transform.

19. A medical telemetry system comprising:
a central station comprising a central station receiver and a central station transmitter, the central station receiver and the central station transmitter operating on a predetermined frequency bandwidth having a plurality of frequency-multiplexed transmission channels and a plurality of guard bands, each of the plurality of frequency-multiplexed transmission channels being separated in frequency by one of the plurality of guard bands, the central station receiver bring is configured for wirelessly receiving patient data from at least one of the plurality of frequency-multiplexed transmission channels and the central station transmitter being configured for wirelessly transmitting control data information via at least one of the plurality of guard bands, the central station receiver comprising:
an antenna selector connected to each of a plurality of antennas for selecting an antenna;
a first IF mixer connected to the antenna for an IF mixer output;
a synthesizer connected to the IF mixer;
a bandpass filter connected to the IF mixer;
a baseband mixer connected to the IF mixer;
an analog to digital converter (ADC) connected to the bandpass filter;
a digital signal processor (DSP) connected to the ADC for generating a DSP output;
a digitally controlled synthesizer coupled to the ADC and DSP;
a second IF mixer connected to the digitally controlled synthesizer for combining the output from the digitally controlled synthesizer and a baseband signal;
a variable phase shifter connected to the second IF mixer and the DSP; and
a summer connected between the bandpass filter, baseband mixer and the variable phase shifter; and
a patient monitor comprising a patient monitor receiver and a patient monitor transmitter, the patient monitor receiver and the patient monitor transmitter operating on at least one of the plurality of frequency-multiplexed transmission channels, the patient monitor wirelessly connected to central station, the patient monitor receiver being configured for wirelessly receiving the control data from the central station transmitter via at least one of the plurality of guard bands and the central station transmitter being configured for wirelessly transmitting the patient data to the central station receiver via at least one of the plurality of frequency-multiplexed transmission channels.

20. The system of claim 19, wherein the central station receiver further comprises an attenuator connected to the antenna selector for attenuating a received signal to a desired level as an output.

21. The system of claim 19, wherein the central station transmitter of the central station transmits the control data information via the plurality of guard bands using multi-carrier modulation (MCM).

22. The system of claim 19, wherein a range of the predetermined frequency bandwidth is selected from the group consisting of 608 to 614 MHz, 1395 to 1400 MHz and 1427 to MHz.

23. The system of claim 19, wherein the predetermined frequency bandwidth comprises about 6 MHz.

24. The system of claim 19, wherein the plurality of frequency-multiplexed transmission channels and the plurality of guard bands comprises 240 channels.

25. The system of claim 19, wherein each of the plurality of frequency-multiplexed transmission channels is spaced about 25 kHz from each other.

26. The system of claim 19, wherein one of the plurality of guard bands comprises a frequency bandwidth of about 25 kHz.

27. The system of claim 19 wherein the central station receiver is configured to use adaptive cancellation for canceling interference caused by the central station transmitter wherein the interference comprises control data being transmitted by the central station transmitter to the patient monitor receiver.

28. The system of claim 19, wherein the patient monitor comprises a plurality of patient monitors and wherein each of the plurality of patient monitors comprise a patient monitor receiver and a patient monitor transmitter.

29. The system of claim 19, wherein the patient monitor receiver is configured to use adaptive cancellation for canceling interference caused by the patient monitor transmitter wherein the interference comprises patient data being transmitted by the patient monitor transmitter to the patient monitor receiver.

30. The system of claim 19, wherein the patient monitor receiver further comprises a filter for filtering interference wherein the interference comprises patient data information being transmitted by others of the plurality of patient monitors.

31. The system of claim 19, wherein the patient monitor receiver comprises:
    an antenna wirelessly connected to the patient monitor receiver for receiving the control data information via at least one of the plurality of guard bands from the central station transmitter;
    an amplifier connected to the antenna for amplifying the received control data information;
    an IF mixer connected to the amplifier to generate a IF signal;
    a synthesizer connected to the IF mixer;
    a bandpass filter connected to the IF mixer;
    an interference reject filter connected to the bandpass filter for rejecting a known frequency of an interference signal; and
    a baseband mixer connected to the interference reject filter for generating a complex baseband signal for processing by the patient monitor.

32. The system of claim 19 wherein the patient monitor receiver comprises a maximal ratio combining filter for estimating a channel frequency response for each of the guard bands and weighting conjugates of the estimated channel frequency responses such that the control data received via each of the guard bands can be combined into a signal control data signal by the patient monitor receiver.

33. The system of claim 32 wherein the estimation of the channel frequency response uses a Hadamard transform.

34. A method of two-way communication in a medical telemetry system comprising the steps of:
    providing a central station transmitter in a central station for communicating to a plurality of individual patient monitors;
    providing a patient monitor receiver in each of the plurality of individual patient monitors for communicating with the central station transmitter;
    operating the central station transmitter and the patient monitor receiver on a predetermined frequency bandwidth having a plurality of frequency-multiplexed transmission channels and a plurality of guard bands, each of the plurality of frequency-multiplexed transmission channels being separated in frequency by one of the plurality of guard bands;
    transmitting control data using the central station transmitter via the plurality of guard bands to each of the plurality of individual patient monitors; and
    receiving the control data at the patient monitor receiver via the plurality of guard bands; and
    processing the received control data at the patient monitor receiver.

35. The method of 34, wherein the step of transmitting control data using the central station transmitter comprises using multi-carrier modulation (MCM).

36. The method of 34, wherein the step of transmitting control data using the central station transmitter comprises sending a sequence of successive data frames, each frame comprising a set of fields.

37. The method of 36, wherein the step of processing the received control data further comprises demodulating a specific field of each frame and identifying the control data for a particular one of the plurality of individual patient monitors.

38. The method of claim 37, wherein demodulating a specific field of each frame for identifying the control data information comprises demodulating other data frames and receiving a signal message when a field has been identified with the particular one of the plurality of individual patient monitors.

39. The method of claim 34 further comprising the steps of:
    providing a central station receiver;
    providing a patient monitor transmitter in each of the plurality of patient monitors;
    operating the central station receiver and the patient monitor transmitter on the predetermined frequency bandwidth using one of the plurality of frequency-multiplexed transmission channels;
    transmitting patient data using the patient monitor transmitter via the one of the plurality of frequency-multiplexed transmission channels; and
    receiving the transmitted patient data at the centrals station receiver.

40. The method of claim 39, further comprising the step of rejecting interference at the patient monitor receiver caused by the transmitted patient data from the patient monitor transmitter.

41. The method of claim 40, wherein the step of rejecting interference caused by the transmitted patient data comprises using adaptive cancellation to cancel the interference.

42. The method of claim 39, further comprising the step of rejecting interference at the patient monitor receiver caused by the transmitted patient data from others of the plurality of patient monitors.

43. The method of claim 42, wherein the step of rejecting interference at the patient monitor receiver comprises using a filter for filtering the interference from the received control data at the patient monitor receiver.

44. The method of claim 39, further comprising the step of rejecting interference at the central station receiver caused by the transmitted control data from the central station transmitter.

45. The method of claim 44, wherein the step of rejecting interference caused by the transmitted control data comprises using adaptive cancellation to cancel the interference.

46. The system of claim 34, wherein a range of the predetermined frequency bandwidth is selected from the group consisting of 608 to 614 MHz, 1395 to 1400 MHz and 1427 to MHz.

47. The system of claim 34, wherein the predetermined frequency bandwidth comprises about 6 MHz.

48. The system of claim 34, wherein the plurality of frequency-multiplexed transmission channels and the plurality of guard bands comprises 240 channels.

49. The system of claim 34, wherein one of the plurality of frequency-multiplexed transmission channels comprises a frequency bandwidth of about 25 kHz.

50. The system of claim 34, wherein each of the plurality of frequency-multiplexed transmission channels is spaced about 25 kHz from each other.

* * * * *